United States Patent [19]

Yagi et al.

[11] 4,228,807
[45] Oct. 21, 1980

[54] BIOFEEDBACK DEVICE FOR RECOGNITION OF α WAVE COMPONENT AND MUSCLE POTENTIAL COMPONENT

[75] Inventors: Akihiro Yagi, Tokyo; Yasuo Kuchinomachi, Yokohama; Hiroyuki Kodama, Tokyo, all of Japan

[73] Assignee: Agency of Industrial Science & Technology, Tokyo, Japan

[21] Appl. No.: 968,263

[22] Filed: Dec. 11, 1978

Related U.S. Application Data

[63] Continuation of Ser. No. 781,362, Mar. 25, 1977, abandoned.

[30] Foreign Application Priority Data

May 27, 1976 [JP] Japan .................................. 51-61528

[51] Int. Cl.³ ............................................. A61B 5/04
[52] U.S. Cl. .................................................. 128/732
[58] Field of Search ................ 128/731, 732, 733, 905

[56] References Cited

U.S. PATENT DOCUMENTS 3,821,949  7/1974  Hartzel et al. ...................... 128/732

*Primary Examiner*—William E. Kamm
*Attorney, Agent, or Firm*—Kurt Kelman

[57] ABSTRACT

Disclosed herein is a biofeedback device which separately extracts the α wave component and the muscle component included in the brain wave and, therefore, permits the user thereof through auditory perception of associated audio frequency sounds to recognize accurately the appearance in the brain wave of the α wave component or muscle component on the basis of the principle that exclusive perception of the sound associated with the α wave component indicates relaxation of the subject's mental state, exclusive perception of the sounds associated with the muscle component indicates tension of the subject's mental state or cephalic state and simultaneous perception of the sounds associated with both components indicates occurrence of a phenomenon having nothing to do with the responses for feedback training.

1 Claim, 2 Drawing Figures

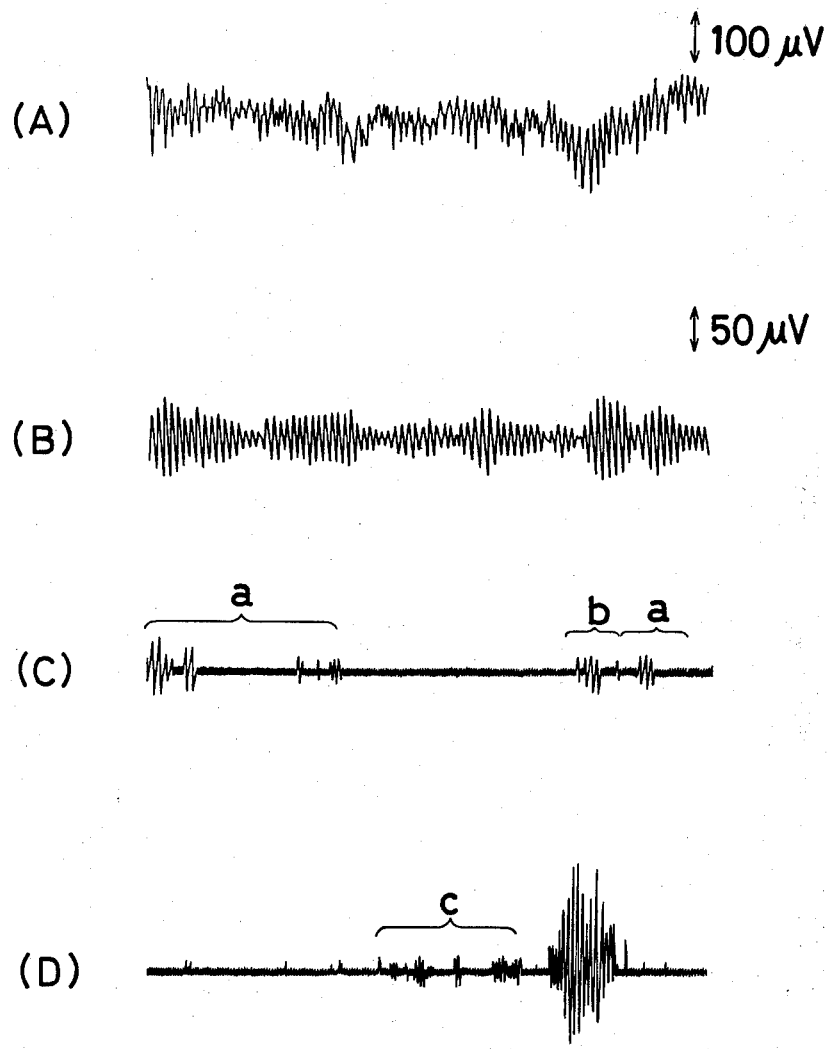

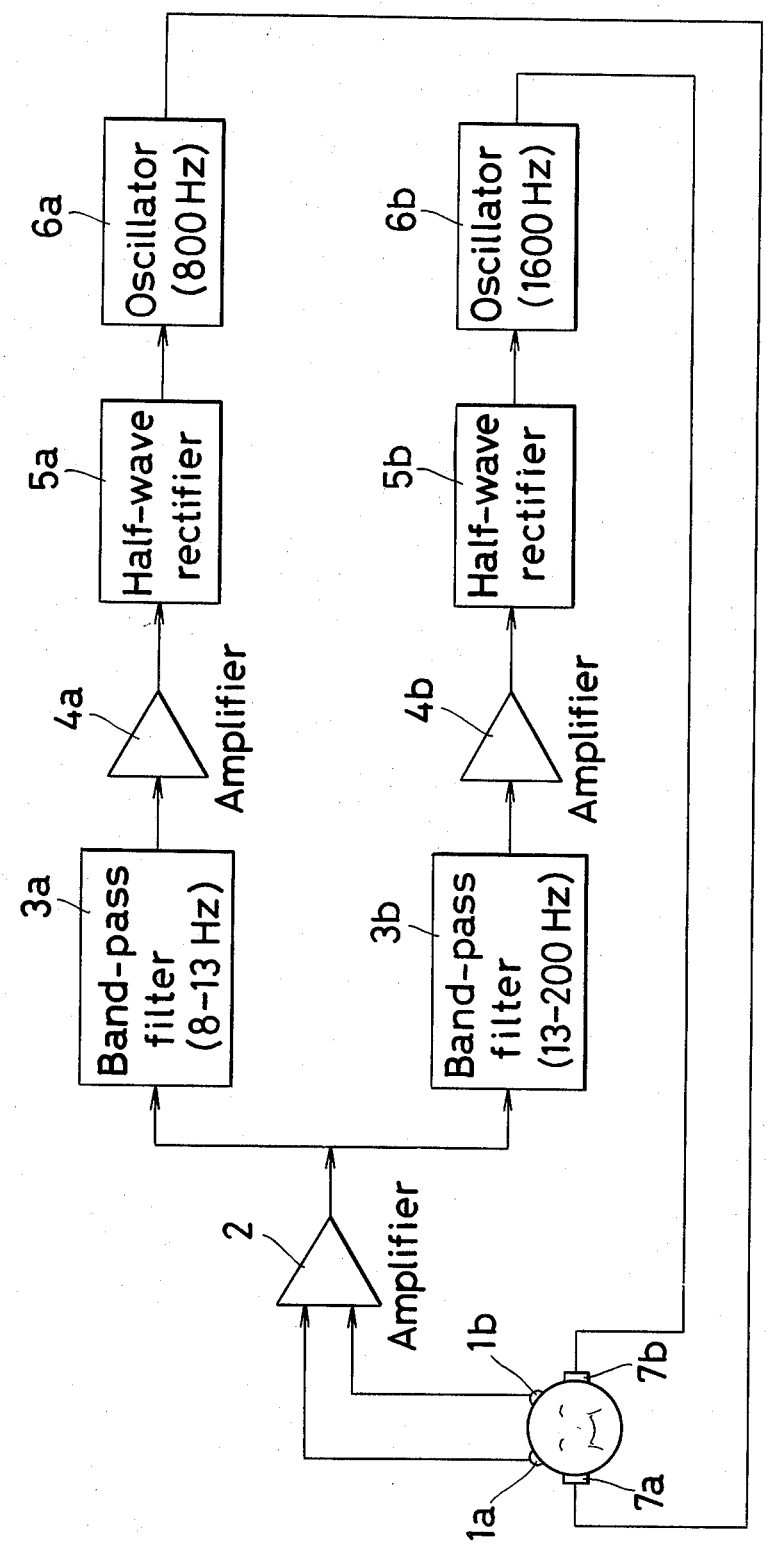

BIOFEEDBACK DEVICE FOR RECOGNITION OF α WAVE COMPONENT AND MUSCLE POTENTIAL COMPONENT

This is a continuation of application Ser. No. 781,362, filed Nov. 25, 1977 now abandoned.

BACKGROUND OF THE INVENTION

This invention relates to a biofeedback device for the recognition of specific frequency components encompassed in the brain wave potential and the muscle potential.

The α component of the brain wave in the frequency band of 8 to 13 Hz constitutes an index of the tranquility of mental state. With a device capable of extracting the α wave component of the brain wave and converting it to an associated audible sound, a person can promote tranquillization of his own mental state by listening to the sound and endeavoring to control his mental activity so as to increase the frequency at which this specific component is generated as sensed by the presence of the associated sound. This endeavor is generally referred to as "biofeedback therapy". Heretofore, psychiatrists and psychologists have trained their patients to improve their ability to generate such specific brain waves as a way of self-control. In this case, for the purpose of exact detection of the frequency components of the wave forms of the brain wave potential and muscle potential, the therapy has inevitably required use of a bulky amplifying apparatus in a laboratory and the patient himself has been compelled to remain at perfect rest during the therapy.

If mere extraction of the specific frequency components of the brain wave and muscle potential were sufficient for the purpose of this therapy, then the measurement could be accomplished with ample accuracy by increasing the S/N ratio to the extent of shutting off the external noise and, at the same time, the apparatus to be used could do without a bulky amplifier and could be greatly reduced in size.

Unfortunately, any attempt at exclusively extracting, through filtration, the α wave component of the frequency band of 8 to 13 Hz from the brain wave is foiled by harmonic interference caused even by the mere movement of the head which mingles into the α wave component. Even the muscle wave form which is generated by the movement of eye lids creates harmonic interference in the α wave component. Exact detection of the α wave component in the brain wave, therefore, cannot be attained by sole use of a wave filter capable of separating the wave of the frequency band of 8 to 13 Hz.

An object of the present invention is to provide a biofeedback device which permits easy recognition of the α wave component of the brain wave only.

Another object of the present invention is to provide a biofeedback device which permits easy recognition of the mental state of a subject and the condition of the subject's cephalic tension with clear distinction.

SUMMARY OF THE INVENTION

To accomplish the objects described above according to the present invention, there is provided a biofeedback device which comprises a pair of electrodes for detecting the brain wave, first and second band-pass filtration means for separately extracting the α wave component and the muscle component from the detected wave form, first and second audo oscillators for producing sounds of different frequency in response to the α wave component extracted by the first band-pass filtration means and the muscle component extracted by the second band-pass filtration means, and means for guiding the sounds from the oscillators to the subject's ears.

The biofeedback device of this invention thus extracts the α wave component and the muscle component separately of each other from the brain wave and produces sounds representing the two components. By listening to these sounds, therefore, the subject can exactly tell his own mental state on the basis of the principle that exclusive perception of the sound representing the α wave component of the brain wave indicates tranquility of the mental state, exclusive perception of the sounds representing the muscle component indicates tension of the mental state and simultaneous perception of the sounds representing both the components indicates occurrence of a phenomenon such as the movement of eye lids or eye balls which is insignificant as an organic reaction. The device, accordingly, enables the subject to precisely identify the generation of the α wave component and, at the same time, to know his own mental state and the tension in the cephalic muscles.

The other objects and characteristic features of the present invention will become apparent from the description given in detail hereinbelow with reference to the accompanying drawings.

BRIEF DESCRIPTION OF THE DRAWINGS

FIG. 1 line (A) shows an electroencephalogram taken of a normal adult.

FIG. 1 line (B) shows the tracing of the α wave component extracted exclusively from the electroencephalogram of FIG. 1 line (A).

FIG. 1 line (C) is a diagram showing the signal transformed from the α wave component of FIG. 1 line (B).

FIG. 1 line (D) is a diagram showing the signal transformed from the muscle potential detected during the recording of said electroencephalogram.

FIG. 2 is a block diagram showing one embodiment of the biofeedback device according to the present invention.

DESCRIPTION OF THE PREFERRED EMBODIMENTS

To facilitate the comprehension of this invention, the α wave component and the muscle component of the brain wave will be explained.

The brain wave represents a change in electric potential caused by the electric activity of the brain, whereas the muscle wave is a change in electric potential produced by the muscular activity.

By way of example, the electroencephalogram taken of a normal adult is shown in FIG. 1 line (A). The tracing of the α wave component extracted from this electroencephalogram is shown in FIG. 1 line (B). The α wave frequency component extracted exclusively from the α wave is shown in FIG. 1 line (C). The form of the muscle wave generated by the movement of the head or by the movement of eye lids or cephalic tension during the recording to the brain wave is shown in FIG. 1 line (D).

In the diagram of FIG. 1 line (C), the portion "a" represents solely the frequency component of the α wave and the portion "b" the frequency component generated by the change in the muscle potential as is plain from FIG. 1 line (D). This means that mere passage of the brain wave through a band-pass filter adapted to separate the wave of the frequency band of 8 to 13 Hz does not always warrant exact exclusive detection of the α wave.

The present invention enables the α wave component and muscle component to be detected separately of each other and, through further treatments of the detected components, determines whether the detected α wave component is genuine or false.

FIG. 2 is a block diagram illustrating one embodiment of the biofeedback device according to the present invention. A pair of detectors 1 adapted to detect the brain wave potential is set in position on the subject's head. Known disc-shaped elctrodes or needle-shaped electrodes are used as the detectors. They may be attached at suitable positions on the cephalic skin, as between the anterior and posterior portions of the head. They may otherwise be pierced into the cephalic skin. Particularly when the detectors are attached on the posterior portion of the head, they are less susceptible of the effect of the muscle component due to the movement of eye balls or eye lids, for example. The brain wave potentials detected by these detectors 1 are amplified by a pre-amplifier 2 and are then forwarded to first and second band-pass filters 3a and 3b respectively. The first band-pass filter 3a is adapted so as to permit exclusive extraction of the component of the wave band of 8 to 13 Hz and the second band-pass filter 3b is adapted to provide exclusive extraction of the component of the wave band exceeding 13 Hz. This means that the α wave component of the brain wave is extracted in the first band-pass filter 3a, whereas the β wave component and the muscle component having wave bands over 13 Hz are extracted in the second band-pass filter 3b.

The α wave component separated off by the first band-pass filter 3a and the β wave component and the muscle component filtered out by the second band-pass filter 3b are forwarded respectively to secondary amplifiers 4a and 4b. In the secondary amplifiers, the signals received therein have their levels adjusted. To be concrete, specific levels are set in advance in the secondary amplifiers. The received signals are compared with the set levels and the portions of the signals exceeding the levels are forwarded. In the case of a subject whose brain wave has a little α wave component, therefore, low levels must be set so that as much α wave as possible will be picked up. In the case of a subject whose brain wave shows the α wave continuously and frequently, high levels must be set so that only the α wave of conspicuous amplitude will be picked up. The respective frequency signals which have undergone the level adjustment as described above are then amplified and forwarded to the half-wave rectifiers 5a and 5b and, with the minus portions of the respective wave forms cut off, forwarded to the oscillators 6a and 6b. The oscillator 6a, for example, is adjusted so as to produce sounds of the frequency of 800 Hz. The oscillator 6b, for example, is adjusted so as to produce sounds of the frequency of 1600 Hz. When the signal of the α wave component is forwarded to the oscillator 6a, the sounds oscillated at the frequency of 800 Hz are perceived by one of the ears through the medium of an earphone 7a. When the signals of the β wave component and the muscle component are forwarded to the oscillator 6b, the sounds oscillated at the frequency of 1600 Hz are perceived by the other ear through the medium of an earphone 7b.

In the biofeedback device of the foregoing construction, the detectors are set in position on the subject's head. The detectors 1 detect the brain wave potential and the cephalic muscle potential. From the wave forms of these potentials, the α wave component of the brain wave and the β wave component and muscle component of the brain wave are respectively extracted. Then, the sounds produced at 800 Hz in response to the appearance of the α wave component of the brain wave are perceived by one of the ears through the medium of the earphone 7a and the sounds produced at 1600 Hz in response to the appearance of the β wave component and muscle component of the brain wave are perceived by the other ear through the medium of the other earphone 7b.

The perception by the one ear of the sounds produced at 800 Hz owing to the appearance of the α wave component of the brain wave of the frequency band of 8 to 13 Hz occurs when there exists a condition corresponding to the portion "a" in FIG. 1 line (C). This is when tranquility prevails in the subject's mental state. The perception by the other ear of the sounds produced at 1600 Hz owing to the appearance of the β wave component and muscle component of the brain wave of the frequency band of 13 to 200 Hz occurs when there exists a condition corresponding to the portion "c" in FIG. 1 line (D). This is when tension prevails in the subject's mental state and/or cephalic muscle condition. The simultaneous perception by the one ear of the sounds produced at 800 Hz and by the other ear of the sounds oscillated at 1600 Hz occurs when there exists a condition corresponding to the portion "b" in FIG. 1 line (C). This is when there occurs a phenomenon which issues from the subject's body motion or some other external disturbance and which is insignificant as an organic reaction. This is because the muscle wave produced by the movement of eye lids or eye balls, the movement of the cephalic skin, and the like mingles directly or in the form of harmonics into the α wave component as already touched upon.

The perception by the one ear of the sounds produced at 800 Hz occurs only when there appears the genuine α wave. The subject, upon simultaneously perceiving the sounds produced at the two frequencies through both ears, can tell that the sounds are not produced in response to the α wave alone. Thus, the subject is permitted to know exactly when the α wave appears in his brain wave.

In the preferred embodiment described so far, the frequency of 800 Hz has been used for the sounds produced in response to the α wave component and the frequency of 1600 Hz for the sounds produced in response to the muscle component. Use of these two different frequencies is intended to permit easy distinction between the occurrence of the α wave component and that of the muscle component. For the generation of such sounds, there may be used other suitable frequencies, therefore, insofar as they satisfy the purpose described. The foregoing embodiment has been described as involving use of earphones adapted to permit the subject to recognize his own mental state. The earphones may be replaced by a speaker. Further, a physician can easily learn the mental state of his patient by listening to the sounds. The sounds produced by the oscillators and heard through the earphones or a speaker are suitable for auditory perception, whereas the outputs of the oscillators may be recorded.

Generally in training an affected person how to obtain tranquility in his mental state, it is difficult to guide his mental state in the direction of increasing the frequency of the appearance of the α wave. By encouraging him to lessen the muscle discharge from the muscle frontalis and consequently minimize the volume of sounds oscillated at 1600 Hz, the frequency of the appearance of the α wave can easily be heightened. This is because elimination of the muscular stress is mentally easier to accomplish than increase of the α wave and the elimination of the muscular stress has an effect of directly aiding in enhancing the α wave.

The biofeedback device of this invention can also be used effectively in a therapy directed to lowering muscular stress. In this case, the subject has only to endeavor to prevent occurrence of sounds oscillated because of the appearance of the muscle wave of the frequency band of 13 to 200 Hz without reference to a change in the frequency of the occurrence of α wave. The detection electrodes are used more effectively in this case when they are attached to the frontal forehead or the shoulder where the muscular stress occurs more readily than elsewhere.

As is clear from the description given above, the biofeedback device of the present invention produces sounds at different frequencies in response to the appearance of the α wave and the muscle component in the brain wave and, therefore, permits the user to recognize the mental state and the muscular condition of the head quite easily and exactly. Furthermore, since it only detects specific frequency components of the brain wave and muscle wave, it has an extremely simple construction. It may be compacted to a pocketable size so as to be readily transported to any desired place chosen for its use.

What is claimed is:

1. A biofeedback device comprising
   (a) a pair of electrodes on the head skin of a subject for detecting a brain wave potential of a frequency of 8 to 13 Hz including an alpha-wave potential and a brain wave potential of a frequency of more than 13 Hz including a muscle potential,
   (b) a first band-pass filter for extracting from the detected potentials a wave component of the frequency of 8 to 13 Hz,
   (c) a second band-pass filter for extracting from the detected potentials a wave component of the frequency of more than 13 Hz,
   (d) a first half-wave rectifier for cutting off the negative component of the wave component extracted by the first band-pass filter,
   (e) a second half-wave rectifier for cutting off the negative component of the wave component extracted by the second band-pass filter,
   (f) a first oscillator for producing a sound of the frequency of 800 Hz and a strength proportional to that of the wave component from the first rectifier,
   (g) a second oscillator for producing a sound of the frequency of 1,600 Hz and a strength proportional to that of the wave component from the second rectifier, and
   (h) a pair of earphones guiding the oscillated sounds simultaneously to the ears of the subject, one of the earphones guiding the sound of the frequency of 800 Hz produced by the first oscillator to one of the ears and another one of the earphones guiding the sound of the frequency of 1600 Hz produced by the second oscillator to the other ear, thereby to permit the subject to discern his own mental state from the strength of the sounds of the frequencies of 800 and 1600 Hz.

* * * * *